(12) United States Patent
Pennemann et al.

(10) Patent No.: US 8,110,073 B2
(45) Date of Patent: Feb. 7, 2012

(54) PROCESS FOR THE PREPARATION OF AROMATIC AMINES

(75) Inventors: Bernd Pennemann, Bergisch Gladbach (DE); Bill Brady, Houston, TX (US); Rainer Buse, Köln (DE)

(73) Assignee: Bayer MaterialScience AG, Leverkusen (DE)

( * ) Notice: Subject to any disclaimer, the term of this patent is extended or adjusted under 35 U.S.C. 154(b) by 847 days.

(21) Appl. No.: 12/001,829

(22) Filed: Dec. 13, 2007

(65) Prior Publication Data

US 2008/0179176 A1 Jul. 31, 2008

(30) Foreign Application Priority Data

Dec. 18, 2006 (DE) .......................... 10 2006 059 678

(51) Int. Cl.
*B01D 3/02* (2006.01)
*C07C 209/36* (2006.01)
*C07C 209/86* (2006.01)

(52) U.S. Cl. ................ 203/14; 203/25; 203/27; 203/29; 203/99; 203/100; 203/DIG. 8; 203/DIG. 19; 564/420; 564/437

(58) Field of Classification Search .................... 203/14, 203/25, 27, 29, 92, 96, 99, 100, DIG. 8, DIG. 19; 564/420, 437

See application file for complete search history.

(56) References Cited

U.S. PATENT DOCUMENTS

| 3,194,839 | A | * | 7/1965 | Robinson et al. | 502/185 |
|---|---|---|---|---|---|
| 4,720,326 | A | | 1/1988 | Beckhaus et al. | 203/14 |
| 4,792,626 | A | | 12/1988 | Becher et al. | 564/422 |
| 5,563,296 | A | * | 10/1996 | Zarnack et al. | 564/422 |
| 5,779,995 | A | | 7/1998 | Witt et al. | 422/215 |
| 6,472,564 | B1 | | 10/2002 | Biskup et al. | |
| 2005/0263385 | A1 | | 12/2005 | Steffens et al. | 203/14 |

* cited by examiner

*Primary Examiner* — Virginia Manoharan
(74) *Attorney, Agent, or Firm* — Lyndanne M. Whalen; Noland J. Cheung

(57) ABSTRACT

Aromatic amines are produced by catalytic hydrogenation of aromatic nitro compounds. The reaction mixture generated by this hydrogenation is then worked up by distillation in a manner which makes it possible to substantially free the amine of water with increased energy efficiency. Water free of amine and low boilers and the low boiling materials are also obtained.

7 Claims, No Drawings

PROCESS FOR THE PREPARATION OF AROMATIC AMINES

BACKGROUND OF THE INVENTION

The present invention relates to a process for the catalytic hydrogenation of aromatic nitro compounds and the working up by distillation of the aqueous amine solutions obtained thereby. In this process, it is possible to substantially free the amine of water in an energy-efficient manner and also to obtain the water free of amine and low boilers and to obtain the low boilers.

It is known, for example from EP-A-0 223 035, that aromatic diamines, such as, for example, toluene diamine (TDA, diaminotoluene), can be prepared by catalytic hydrogenation of the corresponding aromatic dinitro compounds. The hydrogenation can be carried out with the concomitant use of solvents, e.g., low-boiling alcohols such as methanol, ethanol or isopropanol. The hydrogenation is carried out with the aid of catalysts dispersed in the reaction mixture. The dispersed catalysts are subsequently separated off by filtration or sedimentation and are optionally fed back into the process. The hydrogenation reaction is highly exothermic. A constant problem in the hydrogenation of, for example, dinitrotoluene (DNT) to toluenediamine (TDA) is, therefore, not to dissipate this heat as waste heat but to use it expediently. Accordingly, WO-A-96/11052 describes a reaction apparatus for carrying out sludge phase hydrogenations using the heat of reaction to produce usable steam. However, a sufficiently high temperature is essential for the usability of the steam, which in turn requires a correspondingly high reaction temperature.

In EP-A-0223035, for example, steam is produced in a range from 5 to 30 bar. Taking into account the conventional temperature gradients in heat exchangers, a reaction temperature of 160° C. or higher is required to produce such steam. In EP-A-0223035, temperatures in the range from 170 to 250° C. are mentioned.

Working up of the reaction mixture obtained in the hydrogenation has been carried out by freeing a mixture of aromatic diamines and water of reaction that is obtained after removal of the solvent optionally used of water continuously in a distillation column under normal or excess pressure, and then, in further process steps, optionally, freeing the diamine obtained as the distillation residue of adherent water and of any organic compounds that may still be present. Mixtures of water with organic secondary products that are volatile in steam, as are obtained in the hydrogenation of aromatic dinitro compounds, are always obtained as distillates in this procedure. Such secondary products are, for example, aromatic or cycloaliphatic alcohols diaminotoluene, toluidines, methylcyclohexylamines and methylcyclohexyldiamines and/or methylcyclohexanol are being prepared.

The effect of these secondary products that are volatile in steam is that the water distilled via the head is greatly loaded with these compounds. A process for the working up of such aqueous amine solutions by distillation is described in EP-A-0236839. In this disclosed process, the waste water obtained is far less loaded with organic contaminants. To this end, the mixture is separated in a distillation column with sidestream withdrawal. The exhaust vapors of the distillation column are condensed, and the liquid phase obtained thereby is passed over a phase-separation apparatus in which organic secondary products that are volatile in steam are removed from the exhaust vapor condensate as the organic phase. The aqueous phase is fed back at the head of the distillation column. The water, largely freed of organic contaminants that are volatile in steam, is withdrawn via a sidestream. The diamines freed of water and contaminants that are volatile in steam are obtained as the bottom product.

A common feature of all the above-mentioned processes is that the separation by distillation of the water from the TDA- and water-containing reaction mixture obtained in the hydrogenation is carried out at normal or excess pressure, so that the heat obtained in the hydrogenation cannot be used to a substantial degree for the distillation of the TDA- and water-containing reaction mixture due to the temperature level of the steam that is produced. The above-mentioned processes therefore have a high energy consumption in the form of heating steam. From 1.2 to 2 kg of heating steam must be used per kg of water that is to be separated off.

A process that manages with 30 to 50% less heating steam than the other processes of the prior art is described in EP-A-1602640. In this process, a two- or multi-stage column arrangement is used. The pressures and temperatures of the columns are so chosen that the evaporator of the preceding or subsequent column can be operated with the heat released in the condensation of the exhaust vapor stream of a column. For example, an arrangement of two columns is shown, in which the first column is operated with an absolute head pressure of 0.6 bar and the second with an absolute head pressure of 3 bar. The evaporator of the first column is heated with the exhaust vapors of the second column. Major disadvantages of this process, however, are the increased investment needed for an additional column and the pumps, pipelines, instruments, etc. required for operation, as a result of which the economy of the process is reduced. The consumption of heating steam per kg of water that is to be separated off is accordingly about 0.7 to 1.4 kg of heating steam.

SUMMARY OF THE INVENTION

The object of the present invention is, therefore, to find a simple and economical process for the preparation of amines and their working up by distillation, which process is carried out using a small amount of supplied energy.

This and other objects which will be apparent to those skilled in the art are accomplished by using at least a portion of the heat generated by the hydrogenation of an aromatic nitro compound in a column with an absolute head pressure of less than 1 bar to separate water from the hydrogenated reaction mixture.

DETAILED DESCRIPTION OF THE INVENTION

The present invention relates to a process for the preparation of one or more aromatic amines by catalytic hydrogenation of the corresponding aromatic nitro compound(s) and the purification thereof by distillation. In this process, the aromatic nitro compound(s) is/are hydrogenated in the liquid phase at temperatures of from 100 to 200° C. in a reaction apparatus in the presence of a catalyst. A reaction mixture containing amine and water is obtained. Water is separated from the amine- and water-containing reaction mixture by a single distillation step to obtain a purified amine containing water in amounts of less than 20 wt. %, based on the weight of the mixture. At least part of the heat of reaction from the hydrogenation reaction is used to heat the distillation step separating water from the amine- and water-containing reaction mixture. The distillation column is operated with an absolute head pressure of less than 1 bar.

The hydrogenation reaction is carried out at temperatures of from 100 to 200° C., preferably from 120 to 180° C., more preferably from 125 to 170° C. and most preferably from 130 to 160° C., in the presence of one or more catalysts, at pressures of from 5 to 100 bar, preferably from 8 to 50 bar and most preferably from 10 to 35 bar.

Any of the commercially available aromatic nitro compounds may be used as the aromatic nitro compound(s). Aromatic mono- and/or di-amines are preferred. Nitrobenzene, nitrotoluene and dinitrotoluene are particularly preferred.

The reaction apparatus used can be, for example, the sludge phase reactor described in WO-A-96/11052. Other suitable reactors are described, for example, in EP-A-0236935 or U.S. Pat. No. 6,350,911. Of course, it is also possible to use a plurality of identical suitable reaction apparatuses or combinations of different suitable reaction apparatuses.

The catalyst(s) used may be any of the hydrogenation catalysts known to be useful for the catalytic hydrogenation of aromatic nitro compounds. Particularly suitable catalysts are the metals of sub-group 8 of the Periodic System of the Elements or mixtures thereof, which can be applied, for example, to support materials such as carbon or oxides of magnesium, aluminum and/or silicon. Preference is given to the use of Raney iron, cobalt and/or nickel, in particular nickel-containing catalysts such as Raney nickel catalysts, as well as palladium- or platinum-containing catalysts on support materials. The preparation and use of a catalyst for hydrogenation of aromatic nitro compounds such as nitrobenzene, nitrotoluenes, dinitrotoluenes, chlorinated aromatic nitro compounds and others is known and has been described in the prior art. (See, e.g., EP-A-0223035, EP-B-1066111, EP-A-1 512 459)

The use of the heat of reaction in a distillation step can take place either directly or indirectly. The use of the heat of reaction preferably takes place in a heat exchanger, which can be arranged in the reactor itself (for example, inside the reactor or as a cooling jacket) or is connected to the reactor (for example, as an external heat exchanger which is heated by the cooling medium of the reactor or the circulated reactor contents themselves). In the case of direct use, a stream from the bottom of the distillation column used to separate water from the amine- and water-containing mixture is passed through the heat exchanger. In the case of indirect use, a heat transfer medium, for example steam, is used. That is, the heat of reaction is first used to produce steam, for example, and the steam is then used to heat the bottom of the distillation column used to separate water from the amine- and water-containing reaction mixture.

Where steam is to be used, it must be ensured that more heat of reaction is freed in the hydrogenation than is required for heating the distillation. The advantage of producing steam is, then, that the excess heat of reaction can easily be supplied to other uses. These include, for example, the steam stripping of organically loaded aqueous solutions or acids, the preheating of extraction and distillation feeds, and the operation of cooling installations, for example, absorption-type refrigerating machines, as well as numerous possible forms of heating. Examples of possible applications which may be mentioned, without implying any limitation, include: heating of chemical installations, particularly the pipelines and tanks thereof, e.g., by means of heat exchangers; stripping of process water and waste water streams such as those obtained in hydrogenation processes for aniline or TDA preparation; stripping of organically contaminated sulfuric acids obtained in nitration processes such as nitrobenzene or DNT preparation; preheating of feeds to installations in which stripping of organically contaminated acid is carried out; and also heating of boiler feed water.

The steam that is produced generally has an absolute pressure of from 1 to 12 bar, preferably from 1.5 to 8 bar, more preferably from 2 to 6 bar and most preferably from 2 to 5 bar.

Catalyst and dissolved gases are separated from the amine- and water-containing reaction mixture obtained in the hydrogenation of the aromatic nitro compound. The hydrogenation reaction mixture is optionally also freed of solvent. If removal of solvent is carried out, it is in turn advantageously effected using the heat of reaction of the hydrogenation, either directly or indirectly by means of the production of steam. The amine- and water-containing reaction mixture freed of solvent usually has an amine concentration of from 50 to 70 wt. %, preferably from 55 to 65 wt. %, based on the weight of the amine- and water-containing reaction mixture. In addition to the desired amine compounds, the amine- and water-containing reaction mixture usually also contains up to 5 wt. %, preferably from 500 to 5000 ppm, of contaminants of the above-mentioned type that are volatile in steam.

In the process of the present invention, substantial portions of the water and of the contaminants that are volatile in steam (for example, aromatic or cycloaliphatic alcohols) are separated from the amine- and water-containing reaction mixture. At least part of the heat of reaction from the hydrogenation reaction is used to heat the distillation step in which water is removed from the amine- and water-containing reaction mixture. Preferably, at least one of the evaporators is partly heated with steam that has been produced using the heat of reaction from the hydrogenation reaction. The bottom product obtained from the distillation of the amine- and water-containing reaction mixture in a single distillation step contains less than 20 wt. %, preferably less than 10 wt. %, more preferably less than 5 wt. % and most preferably less than 3 wt. % water, based on the weight of the purified water-containing amine.

In this manner, preferably at least 50%, most preferably at least 60%, of the energy requirement for the distillation of the amine- and water-containing reaction mixture is satisfied by heating with the heat of reaction from the hydrogenation reaction. The use of additional fresh steam is therefore markedly reduced. This is possible because of the distillation at an absolute head pressure below 1 bar and the resulting low temperature level in the distillation.

In a single distillation step, the water is removed from the amine- and water-containing reaction mixture, which usually has amine concentrations of from 55 to 70 wt. % and water concentrations of from 30 to 45 wt. %, based on the weight of the amine- and water-containing reaction mixture, to such an extent that the above-mentioned water contents are obtained. However, this does not exclude the possibility, for example, of portions of water already being separated from the amine- and water-containing reaction mixture in the solvent separation that optionally takes place beforehand, or of water being removed from the purified amine in further distillation steps carried out subsequently.

The evaporator is not subject to any limitations and any of the known evaporators is suitable for use in the process of the present invention. It is possible, for example, to use the forced or natural circulation evaporators which are conventional in the art, or internal or external heating bundles located inside the column. In particular, combinations of a plurality of identical or different evaporators can be used. In that case, at least one of the evaporators is to be operated with the heat of the hydrogenation reaction and is preferably to be constructed so that the heat of the hydrogenation reaction supplies at least 50% of the total capacity of the evaporators of the distillation step. In another embodiment of the process of the present invention, part or all of the bottom stream leaving the column is passed through the heat exchanger connected to the hydrogenation reactor and heated directly by the heat of reaction. The column can be in the form of, for example, a bubble tray or packed column, the column having from 12 to 50, preferably from 20 to 40, theoretical plates. The column is operated with an absolute head pressure of less than 1 bar, preferably from 0.3 to 0.8 bar. The amine- and water-containing reaction mixture that is to be separated is preferably applied above the evaporator, most preferably between the second and the eighth theoretical plates. The exhaust vapors of the column are condensed, and a portion thereof is applied to the column as reflux, the reflux ratio preferably being at least 0.2, most preferably from 0.3 to 0.6.

In a further embodiment of the process of the present invention, an organic phase that is volatile in steam is separated off and the aqueous phase is again applied at the head of the column. The withdrawal of the distillate, that is to say the withdrawal of the water, preferably takes place via a sidestream which is arranged at least 4, preferably from 5 to 15, theoretical plates beneath the head of the column and at least 8, preferably from 15 to 25, theoretical plates above the bottom of the column. The volume ratio of reflux (beneath the withdrawal site) to the withdrawal of the water is preferably at least 0.2, most preferably from 0.3 to 0.6.

The major advantage of the process of the present invention is, therefore, that the heat of reaction obtained in the hydrogenation, even at low temperatures, can be used for the separation of water from the amine- and water-containing reaction mixture that is produced. This is made possible by the distillation at absolute pressures of <1 bar, in which the water is largely removed from the TDA in only a single step. As a result, it is possible, as illustrated by means of the example, to carry out the distillation with amounts of external steam of less than 0.6 kg of steam per kg of water separated off. (In the Example, 0.45 kg of heating steam per kg of water are separated off). External steam means steam that is not obtained from the heat of reaction of the hydrogenation. This represents a saving of more than 50% as compared with the prior art processes.

This savings was not possible with the processes according to the prior art because the separation of water by distillation has conventionally been carried out at normal or excess pressure and accordingly at high temperatures, and the temperature level of the steam produced at low hydrogenation temperatures of from 100 to 200° C. is not sufficient.

In the only known process in which a reduced pressure is used for the distillation, it is necessary according to the teaching of EP-A-1602640 to combine a plurality of mutually connected distillation columns, which are, however, likewise operated without the use of the heat from the hydrogenation. According to the teaching of EP-A-1602640, the evaporator of the column operated at low pressures and accordingly also at low temperatures is heated with the exhaust vapors from the column operated at higher pressures and accordingly at higher temperatures, so that there is no possibility at all of using the heat of hydrogenation in a distillation column operated at reduced pressure.

EXAMPLES

A DNT isomeric mixture was hydrogenated in a reactor at 130° C. and a pressure of 22 bar. The heat of reaction was dissipated via an internal heat exchanger in which water was evaporated at a pressure of 1.5 bar absolute. The reaction mixture was filtered and relieved to normal pressure. The mixture was an approximately 60 wt. % solution (based on the weight of the reaction mixture) of a diamine mixture consisting substantially of 77.2 wt. % 2,4-diaminotoluene, 19.3 wt. % 2,6-diaminotoluene and 3.5 wt. % of other diaminotoluene isomers, in each case based on the sum of the weights of the diaminotoluene isomers. The solution had a content of organic secondary products that are volatile in steam of 0.3 wt. %. The water content of the solution was accordingly about 39.7 wt. %, based on the weight of the reaction mixture. The mixture was then distilled in a column having 30 stages. The feed was admitted at the 5th stage above the bottom. The column was operated at an absolute head pressure of 400 mbar. The column had two evaporators, the bottom of the column terminating in the first evaporator. A portion of the bottom stream was evaporated in the first evaporator and fed back into the column; the other portion flowed via an overflow into the second evaporator. A portion of the stream that had overflowed into the second evaporator was evaporated in the second evaporator and fed back into the column, the other portion is discharged as the product stream (purified amine). The first evaporator was operated with the steam of 1.5 bar from the hydrogenation reaction. The second evaporator was operated with steam from another source, the temperature of this steam was 170° C. The temperature in the outlet of the first evaporator was 90°, the water content was about 19.5 wt. %. The second evaporator was operated with an outlet temperature of 120° C., a water content of 2 wt. % being established. The product stream (purified amine) discharged from the second evaporator contained water in a concentration of 2 wt. %. The reflux ratio at the head of the column was 0.5. The proportion of heat of hydrogenation introduced via the first evaporator to the total energy required for the separation in both evaporators was 72%.

The amount of external steam required for the separation in the column used was only 0.45 kg per kg of water expelled.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of an aromatic amine by catalytic hydrogenation of the corresponding aromatic nitro compound and the purification thereof by distillation comprising:
   a) hydrogenating the aromatic nitro compound in liquid phase at a temperature of from 100 to 200° C. in a reaction vessel in the presence of a catalyst to form a reaction mixture containing amine and water and to generate heat,
   b) separating water from the reaction mixture containing amine and water by a single distillation in a distillation column to obtain a purified amine containing water in an amount of less than 20 wt. %, based on the weight of the mixture,
   c) using at least a portion of the heat from the hydrogenation of step a), either directly or indirectly, to heat the distillation in step b), and
   d) operating the distillation column with an absolute head pressure of less than 1 bar.

2. The process of claim 1 in which the heat generated in step a) is used to convert water to steam and this steam is then used to heat the distillation in step b).

3. The process of claim 2 in which the steam produced has an absolute pressure of from 1 to 12 bar.

4. The process of claim 2 in which the heat generated in step a) supplies sufficient energy to satisfy at least 50% of the energy requirement of the distillation in step b).

5. The process of claim 1 in which the aromatic nitro compound is nitrobenzene, nitrotoluene or dinitrotoluene.

6. The process of claim 1 in which the water is removed as a sidestream in the single distillation step.

7. The process of claim 1 in which the heat generated in step a) supplies sufficient energy to satisfy at least 50% of the energy requirement for the distillation in step b).

* * * * *